United States Patent
Lee et al.

(10) Patent No.: US 10,818,066 B2
(45) Date of Patent: Oct. 27, 2020

(54) VISUALIZATION METHOD AND DEVICE FOR MULTI-DIMENSIONAL DATA ANALYSIS

(71) Applicant: AJOU UNIVERSITY INDUSTRY-ACADEMIC COOPERATION FOUNDATION, Suwon-si (KR)

(72) Inventors: Kyung Won Lee, Seoul (KR); Hyo Ji Ha, Seoul (KR); Hyun Woo Han, Suwon-si (KR); Sung Yun Bae, Seongnam-si (KR); Ji Hye Lee, Bucheon-si (KR); Chang Hyung Hong, Seongnam-si (KR); Sang Joon Son, Seoul (KR); Hyun Jung Shin, Seongnam-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 15/821,981

(22) Filed: Nov. 24, 2017

(65) Prior Publication Data

US 2018/0144534 A1     May 24, 2018

(30) Foreign Application Priority Data

Nov. 24, 2016    (KR) ........................ 10-2016-0157400
Feb. 17, 2017    (KR) ........................ 10-2017-0021701

(51) Int. Cl.
    *G06T 15/00*       (2011.01)
    *G06T 11/20*       (2006.01)
    (Continued)

(52) U.S. Cl.
    CPC .............. *G06T 15/00* (2013.01); *G06F 16/00* (2019.01); *G06K 9/6218* (2013.01);
    (Continued)

(58) Field of Classification Search
    CPC ...................................................... G06T 15/00
    (Continued)

(56) References Cited

U.S. PATENT DOCUMENTS

| | | | |
|---|---|---|---|
| 2005/0128199 A1* | 6/2005 | Brooks | G05B 11/32 345/440 |
| 2016/0098173 A1* | 4/2016 | Slawinski | G06F 16/904 715/739 |

OTHER PUBLICATIONS

Cvek, Urska & Trutschl, Marjan & Stone II, R & Syed, Zanobia & Clifford, John & Sabichi, Anita. (2009). Multidimensional Visualization Tools for Analysis of Expression Data. World Acad Sci Eng Technol. 54. (Year: 2009).*

(Continued)

*Primary Examiner* — Shivang I Patel
(74) *Attorney, Agent, or Firm* — Sughrue Mion, PLLC

(57) ABSTRACT

Provided is a method of visualizing a plurality of nodes respectively including a plurality of variable values for a data object. The method includes: allocating a predetermined upper limit value and a predetermined lower limit value for each of a plurality of variables to vertices of a three-dimensional polygon facing each other; respectively determining partial positions related to the variables for the nodes based on the upper limit value and the lower limit value for each of the variables, a maximum variable value and a minimum variable value for each variable from among variable values of the nodes, and the variable values of the nodes; respectively determining final positions of the nodes in the three-dimensional polygon based on the determined partial positions; and arranging the nodes in the three-dimensional polygon according to the determined final positions.

13 Claims, 15 Drawing Sheets
(6 of 15 Drawing Sheet(s) Filed in Color)

(51) Int. Cl.
    *G06T 19/00* (2011.01)
    *G06K 9/62* (2006.01)
    *G06F 16/00* (2019.01)
    *G16H 50/70* (2018.01)
(52) U.S. Cl.
    CPC ............ *G06T 11/206* (2013.01); *G06T 19/00* (2013.01); *G16H 50/70* (2018.01)
(58) Field of Classification Search
    USPC ........................................................ 345/419
    See application file for complete search history.

(56) References Cited

OTHER PUBLICATIONS

Heinrich, J., & Weiskopf, D. (2013). State of the Art of Parallel Coordinates. Eurographics (Year: 2013).*
Urska Cvek et al., "Multidimensional Visualization Tools for Analysis of Expression Data", World Academy of Science, Engineering and Technology, International Journal of Computer, Electrical, Automation, Control and Information Engineering, 2009, vol. 3, No. 6.
Amin Ibrahim et al., "3D-RadVis: Visualization of Pareto Front in Many-Objective Optimization", Accepted for presentation at WCCI-2016, Jul. 25-29, 2016, Vancouver, Canada.

* cited by examiner

FIG. 1
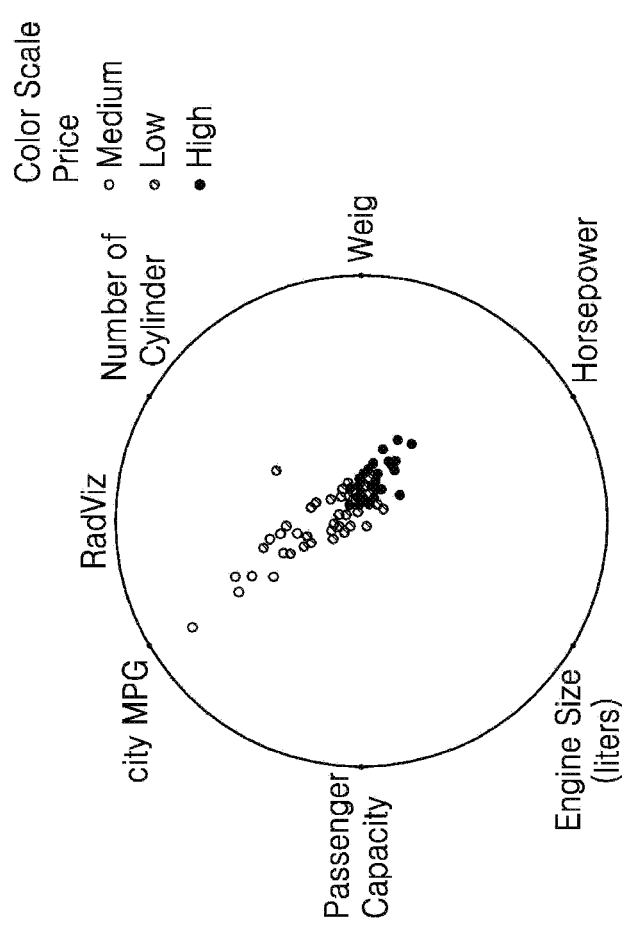
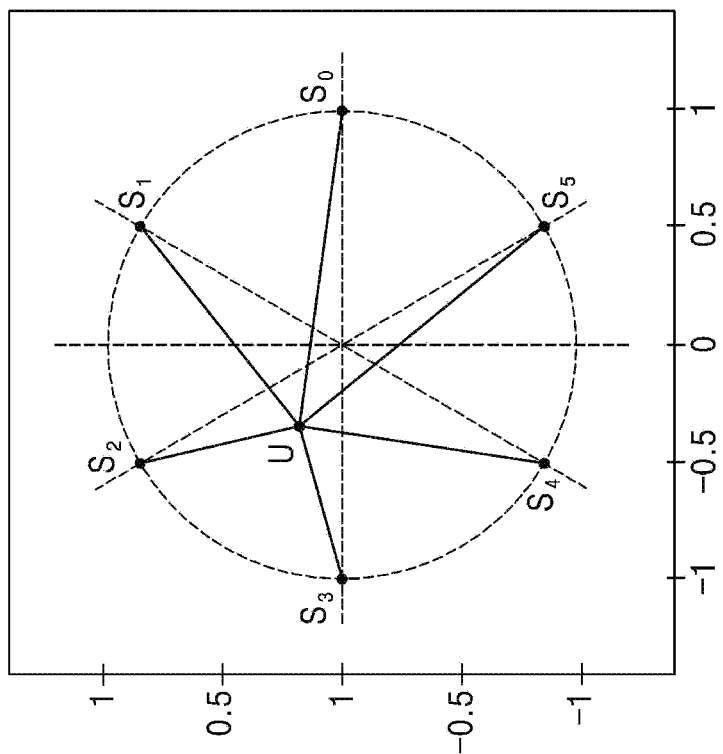

VISUALIZATION METHOD AND DEVICE FOR MULTI-DIMENSIONAL DATA ANALYSIS

CROSS REFERENCE TO RELATED APPLICATIONS

This application claims priority from Korean Patent Application No. 10-2016-0157400, filed on Nov. 24, 2016, and Korean Patent Application No. 10-2017-0021701, filed on Feb. 17, 2017, in the Korean Intellectual Property Office, the contents of which are incorporated herein by reference in their entireties.

BACKGROUND

1. Field

One or more example embodiments relate to a visualization method and a device therefor, and more particularly, to a method and a device for visualizing multi-dimensional data.

The present invention is derived from research conducted as Interdisciplinary Research supported by the National Research Foundation of Korea (NRF) grant funded by the Korea government (MSIP) (No. 2015S1A5B6037107).

2. Description of the Related Art

Multi-dimensional data refers to data containing large amounts of variables, and various studies have been conducted to efficiently refine and analyze the data. Among them, visualization using multi-dimensional data is required to reduce dimensions of data and to present semantic characteristics of the data as much as possible. Therefore, an analysis of cluster units is mainly performed when multi-dimensional data is visualized, and a "clustering" technique from among data mining techniques is frequently used for this purpose. Clustering is a technique of refining multi-dimensional data according to characteristics by classifying the data according to attributes and similarities of the data.

However, existing clustering techniques do not show meaningful results in some clusters in a process of clustering data. For example, assuming that the number of groups to divide is set and then a clustering analysis is performed, some clusters cannot interpret characteristics of data semantically because the number of individuals in the clusters is very small. In this case, a user has to re-designate the number of clusters in order to obtain an optimum clustering result. Therefore, a visualization method that can solve these problems is needed.

SUMMARY

One or more example embodiments include a method and a device for visualizing multi-dimensional data enabling a user to more easily analyze multi-dimensional data.

One or more example embodiments include a method and a device for visualizing multi-dimensional data capable of effectively clustering multi-dimensional data.

Additional aspects will be set forth in part in the description which follows and, in part, will be apparent from the description, or may be learned by practice of the presented example embodiments.

According to an aspect of the inventive concept, there is provided a method of visualizing a plurality of nodes respectively comprising a plurality of variable values for a data object, the method comprising: allocating a predetermined upper limit value and a predetermined lower limit value for each of a plurality of variables to vertices of a three-dimensional polygon facing each other; respectively determining partial positions related to the variables for the nodes based on the upper limit value and the lower limit value for each of the variables, a maximum variable value and a minimum variable value for each variable from among variable values of the nodes, and the variable values of the nodes; respectively determining final positions of the nodes in the three-dimensional polygon based on the determined partial positions; and arranging the nodes in the three-dimensional polygon according to the determined final positions.

According to example embodiments, the determining of the partial positions may include respectively determining the partial positions related to the variables for the nodes according to the following equation.

$$Np_{(i)} = \frac{N_{(i)} - V\min_{(i)}}{V\max_{(i)} - V\min_{(i)}} \times (P\max_{(i)} - P\min_{(i)}) + P\min_{(i)}$$

where, $Np_{(i)}$ is a partial position related to an $i^{th}$ variable of any one of the nodes, $N_{(i)}$ is an $i^{th}$ variable value of any one of the nodes, $V\max_{(i)}$ is a maximum value from among respective $i^{th}$ variable values of the nodes, $V\min_{(i)}$ is a minimum variable value from among respective $i^{th}$ variable values of the nodes, $P\max_{(i)}$ is an upper limit value for the $i^{th}$ variable, and $P\min_{(i)}$ is a lower limit value for the $i^{th}$ variable.

According to example embodiments, the determining of the final positions may include respectively determining the final positions of the nodes in the three-dimensional polygon according to the following equation.

$$Np = \left(\sum_{i=1}^{c} Np_{(i)}\right) \div c$$

where, Np is a final position of any one of the nodes, i is any one of the variables, c is the number of the variables, and $Np_{(i)}$ is a partial position related to an $i^{th}$ variable of any one of the nodes.

According to example embodiments, the allocating to the vertices may include selecting the variables by a user.

According to example embodiments, the allocating to the vertices may include allocating an upper limit value and a lower limit value for any one of the variables to an upper vertex and a lower vertex connected to each other by a side in the three-dimensional polygon, respectively.

According to example embodiments, the method may further include displaying variable values included in the nodes in a parallel coordinate graph.

According to example embodiments, the displaying in the parallel coordinate graph may include receiving a filtering range for at least one variable from a user; and displaying variable values included in the filtering range from among the variable values included in the nodes in the parallel coordinate graph.

According to example embodiments, the filtering range may be plural.

According to example embodiments, the method may further include receiving the number of clusters from a user; clustering the nodes arranged in the three-dimensional polygon according to the received number of the clusters; and displaying the plurality of nodes that are clustered to be distinguished from each other.

According to example embodiments, the clustering may include arbitrarily clustering the nodes arranged in the three-dimensional polygon according to the received number of the clusters; updating a plurality of preliminary clusters based on distances between respective center points of a plurality of preliminary clusters that are arbitrarily clustered and the nodes arranged in the three-dimensional polygon; and repeatedly updating the plurality of preliminary clusters by comparing center points of the plurality of updated preliminary clusters with the center points of the plurality of preliminary clusters before updating, respectively.

According to example embodiments, the repeatedly updating may include repeatedly updating each of the plurality of preliminary clusters until the center point of each of the plurality of preliminary clusters is not changed.

According to example embodiments, the method may further include re-clustering nodes included in clusters selected from among the clusters, and displaying the nodes that are re-clustered as sub-clusters to be distinguished from each other.

According to example embodiments, the re-clustering may include receiving the number of the sub-clusters from the user, and re-clustering the nodes included in the cluster selected from the clusters according to the received number of the sub-clusters.

According to another aspect of the inventive concept, there is provided a device for visualizing a plurality of nodes respectively comprising a plurality of variable values for a data object, the device comprising: a three-dimensional polygon generator configured to allocate a predetermined upper limit value and a predetermined lower limit value for each of a plurality of variables to vertices of a three-dimensional polygon facing each other; a position determiner configured to determine partial positions related to the variables for the plurality of nodes, respectively, and to determine a final position of each of the nodes in the three-dimensional polygon based on the determined partial positions; and a controller configured to arrange the nodes in the three-dimensional polygon according to the determined final positions.

According to example embodiments, the position determiner may be configured to respectively determine the partial positions related to the variables for the nodes based on the upper limit value and the lower limit value for each of the variables, a maximum variable value and a minimum variable value for each variable from among variable values of the nodes, and the variable values of the nodes, and to respectively determine the final positions of the nodes in the three-dimensional polygon based on the determined partial positions.

According to example embodiments, the device may further include a display configured to display the three-dimensional polygon in which the nodes are arranged.

BRIEF DESCRIPTION OF THE FIGURES

The patent or application file contains at least one drawing executed in color. Copies of this patent or patent application publication with color drawing(s) will be provided by the Office upon request and payment of the necessary fee. These and/or other aspects will become apparent and more readily appreciated from the following description of the example embodiments, taken in conjunction with the accompanying drawings in which:

FIG. 1 is a view for explaining a general radial coordinate visualization (RadVis) method;

DETAILED DESCRIPTION OF THE EXEMPLARY EMBODIMENTS

Figure 2:
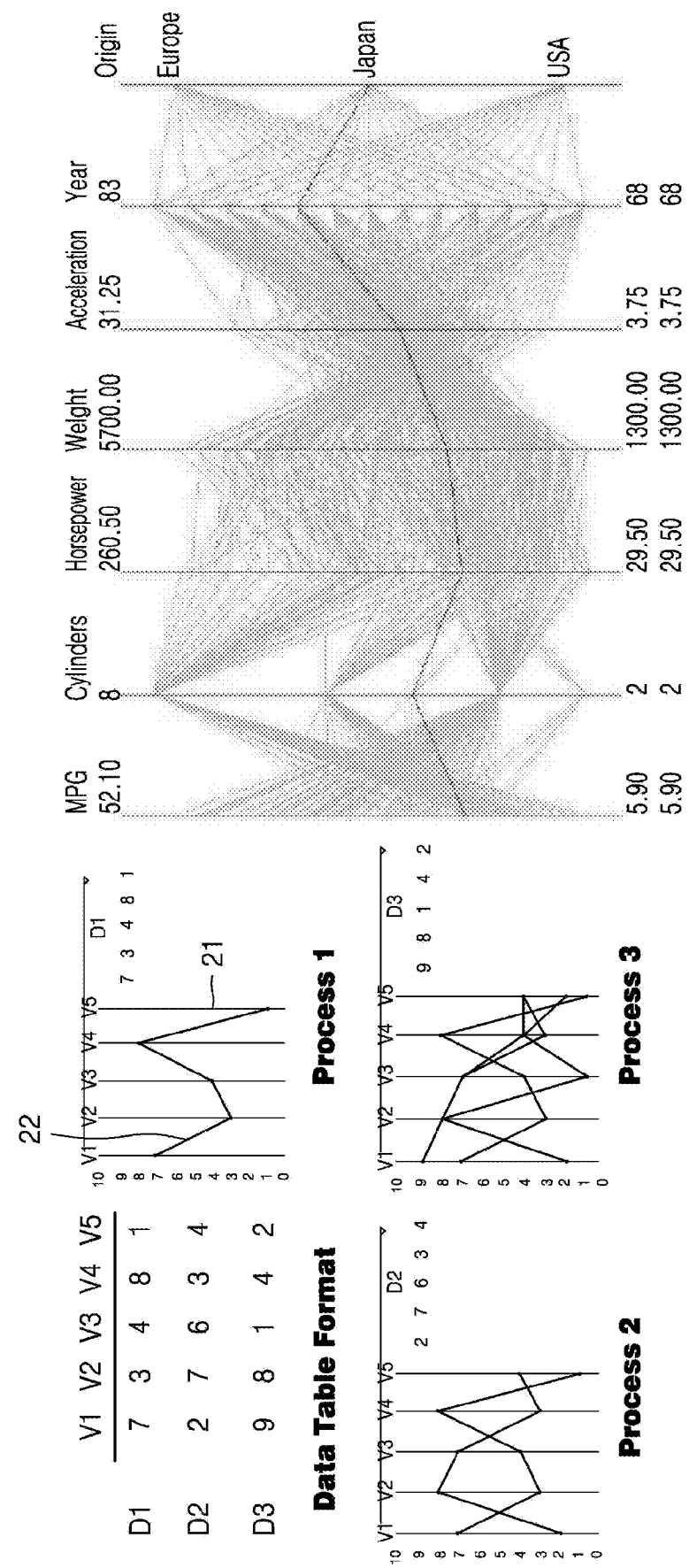
FIG. 2 is a view for explaining a general parallel coordinate visualization method.

Reference will now be made in detail to example embodiments, examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. Expressions such as "at least one of," when preceding a list of elements, modify the entire list of elements and do not modify the individual elements of the list.

In describing the inventive concept, in the following description, a detailed explanation of known related technologies may be omitted to avoid unnecessarily obscuring the subject matter of the inventive concept. In addition, numeral figures (for example, 1, 2, and the like) used during describing the specification are just identification symbols for distinguishing one element from another element.

Further, in the specification, if it is described that one component is "connected" or "accesses" the other component, it is understood that the one component may be directly connected to or may directly access the other component but unless explicitly described to the contrary, another component may be "connected" or "access" between the components.

In addition, terms including "unit", "er", "or", "module", and the like disclosed in the specification mean a unit that processes at least one function or operation and this may be implemented by hardware or software such as a processor, a microprocessor, a micro controller, a central processing unit (CPU), a graphics processing unit (GPU), an accelerated Processing unit (APU), a digital signal processor (DSP), an application specific integrated circuit (ASIC), and a field programmable gate array (FPGA) or a combination of hardware and software.

Moreover, it is intended to clarify that components in the specification are distinguished in terms of primary functions of the components. That is, two or more components to be described below may be provided to be combined to one component or one component may be provided to be divided into two or more components for each more subdivided function. In addition, each of the respective components to be described below may additionally perform some or all functions among functions which other components take charge of in addition to a primary function which each component takes charge of and some functions among the primary functions which the respective components take charge of are exclusively charged by other components to be performed, of course.

Hereinafter, example embodiments of the inventive concept will be described in detail.

Visualization techniques for a data clustering analysis may represent a clustering result by a network, or by using two-dimensional (2D) radial coordinate visualization (RadVis) method or a parallel coordinate method.

FIG. 1 is a view for explaining a general RadVis method.

RadVis is a visualization method that can show a distribution of nodes in a plane where various variables are expressed by reducing a dimension of data using Hook's law to map n-dimensional points to the plane. Referring to a left side of FIG. 1, points $S_0$ to $S_5$. around a circle are points called dimension anchors of RadVis, and variables of the data are located at the points $S_0$ to $S_5$, respectively. Point U is a node represented in the circle, and a position of the node is defined by a tension for each variable value. Therefore, the larger the variable values of the data, the closer the position of the node is to a dimension anchor of each variable around the circle. Accordingly, it can be seen that the node U has a higher value for $S_2$ and $S_3$ variables. RadVis visualization may help to identify a relationship between data depending on density of nodes. It is also characterized in that characteristics of data are provided as a pattern.

However, in the RadVis method, if the number of variables forming RadVis is increased and the nodes are pulled in various directions, a problem that most of the nodes converge at the center cannot be solved. For this reason, conventional techniques for dealing with RadVis sometimes limit the number of variables in a process of reducing the dimension of data. In addition, it is troublesome to perform clustering several times in order to give an optimal meaning to each cluster.

FIG. 2 is a view for explaining a general parallel coordinate visualization method.

The parallel coordinate visualization method is designed to effectively show a set of data in an n-dimensional space. In general, assuming that the number of variables is n, a left side of FIG. 2 shows that axes 21 constituting a parallel coordinate includes n lines are parallel to each other and arranged at an equal distance. One line 22 is a result of connecting each of the axes 21 according to values of respective variables in one piece of data. Referring to a right side of FIG. 2, the parallel coordinate may be interpreted as a similar relationship between two dimensions when most lines of each variable are parallel. Also, when most lines intersect, it can be interpreted as a different relationship.

It is difficult to apply the parallel coordinate to a situation where cluster distribution of data and details of the data need to be seen together.

A visualization method of multi-dimensional data according to an example embodiment provides meaningful information about multi-dimensional data to a user through data visualization by three-dimensional (3D) RadVis and by the parallel coordinate.

Hereinafter, example embodiments will be described with reference to FIG. 3.

Figure 3:
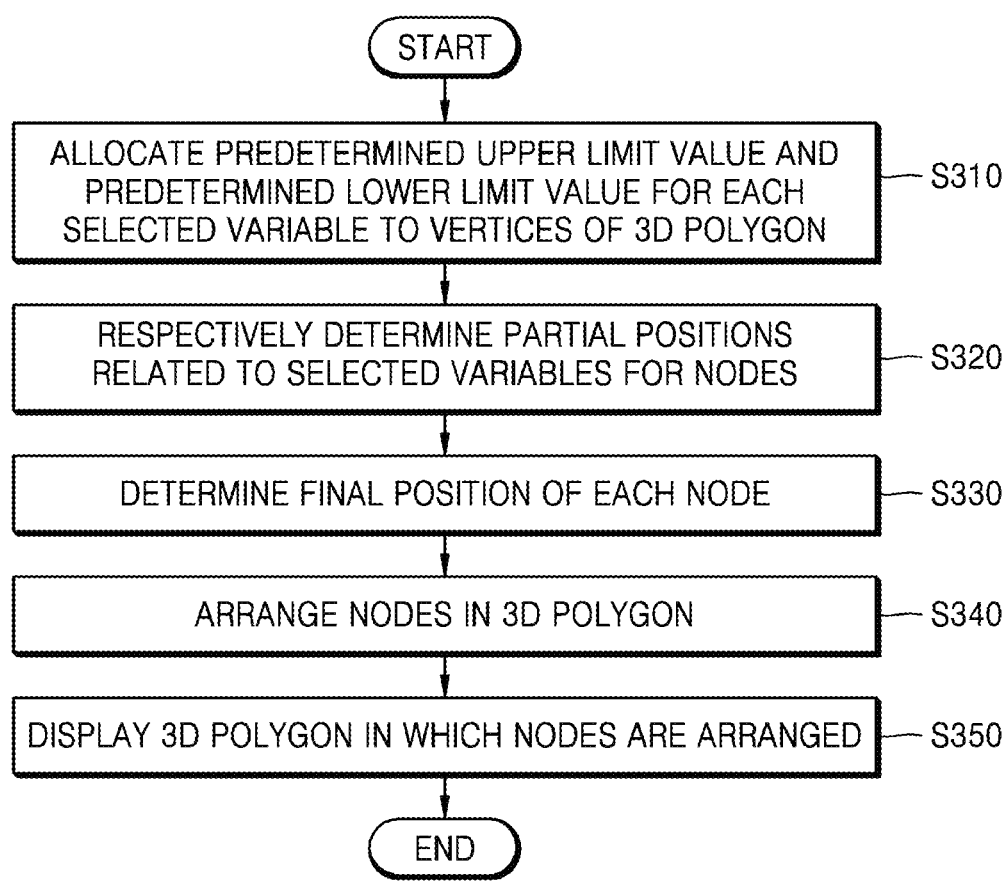
FIG. 3 is a flowchart of a visualization method according to an example embodiment.

FIG. 3 is a flowchart of a visualization method according to an example embodiment.

Each operation in FIG. 3 may be performed by a visualization device. According to an example embodiment, the visualization device may be implemented, for example, as a general-purpose computer, or may include various kinds of devices including a data input unit, a data processing unit, and a data output unit.

The visualization device may pre-store data for visualization, or may receive data via a user or a network. The data may include a set of nodes each containing a numerical value for a plurality of variables for at least one data object, for example, a variable value.

In an example embodiment, 'node' is an object of data, 'variable' is a type of a variable value included in data, and 'variable value' is a value corresponding to a specific variable. For example, if the data is about a cohort diagnosed with dementia of a clinical research center for dementia of South Korea (CREDOS), the 'node' may refer to a particular patient. The 'variable' may mean variables related to patient's personal information such as an age, gender, years of education, or an educational background, variables related to physical examination results such as cholesterol (general, high density lipoprotein (HDL), low density lipoprotein (LDL)), Apolipoprotein E (ApoE) genes, or vitamin B12, and variables related to psychological tests such as Korean dementia screening questionnaire (KDSQ), caregiver-administered neuropsychiatric inventory (CGA-NPI), or Barthel Index for activities of daily living (Barthel-ADL). The 'variable value' may be a numerical value of the above-mentioned variables.

In operation S310, the visualization device allocates a predetermined upper limit value and a predetermined lower limit value for at least one of a plurality of variables (hereinafter, "selected variable") to vertices of a 3D polygon.

The visualization device may select at least one of the variables included in the plurality of nodes by a user. For example, if each of the plurality of nodes includes the variable value corresponding to the variables related to patient's personal information, the variables related to physical examination results, and the variables related to psychological tests, some of the variables may be selected by the user.

The visualization device may form a 3D polygon according to the number of the selected variables. For example, if the number of the selected variables is three, the 3D polygon may be composed of a triangular pillar, and if the number of the selected variables is four, the 3D polygon may be composed of a square pillar.

A predetermined upper limit value and a predetermined lower limit value of each of the selected variables are previously set. For example, in a case of height from among patient's physical examination results, the predetermined upper limit value may be previously set to 200 cm and the predetermined lower limit value may be previously set to 100 cm.

When allocating the predetermined upper limit value and the predetermined lower limit value to the vertices of the 3D polygon, the visualization device may arrange the predetermined upper limit value and the predetermined lower limit value for any one of the variables at an upper vertex and a lower vertex connected to each other by a side on the 3D polygon, respectively.

Figure 4:
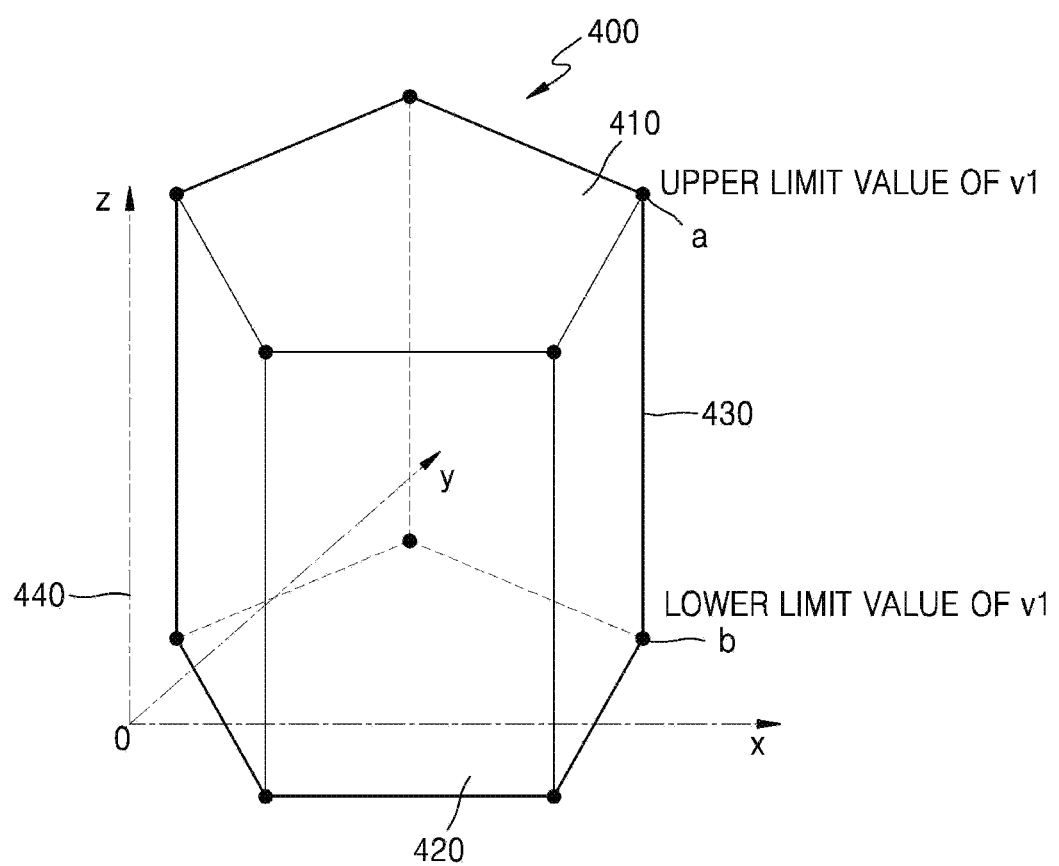
FIG. 4 is an exemplary view of a three-dimensional (3D) polygon according to an example embodiment.

FIG. 4 illustrates a 3D polygon 400 in the shape of a pentagonal pillar. Referring to FIG. 4, it can be seen that one of variables, for example, an upper limit value and a lower limit value of a variable v1 are arranged at a vertex a of an upper surface 410 and a vertex b of a lower surface 420 connected to each other by a side 430, respectively.

Referring again to FIG. 3, in operation S320, the visualization device determines partial positions related to selected variables for the nodes, respectively. For example, if height, weight, and blood pressure from among the patient's physical examination results are arranged as selected variables at the vertices of the 3D polygon, the visualization device may determine respective partial positions related to the height, weight, and blood pressure for each of the nodes.

In more detail, the visualization device may determine the respective partial positions of the nodes according to Equation 1 below.

$$Np_{(i)} = \frac{N_{(i)} - V\min_{(i)}}{V\max_{(i)} - V\min_{(i)}} \times (P\max_{(i)} - P\min_{(i)}) + P\min_{(i)} \quad \text{[Equation 1]}$$

wherein, $Np_{(i)}$ is a partial position related to an $i^{th}$ variable of any one of the nodes, $N_{(i)}$ is an $i^{th}$ variable value of any one of the nodes, $V\max_{(i)}$ is a maximum value from among respective $i^{th}$ variable values of the nodes, $V\min_{(i)}$ is a minimum variable value from among respective $i^{th}$ variable values of the nodes, $P\max_{(i)}$ is an upper limit value for the $i^{th}$ variables, and $P\min_{(i)}$ is a lower limit value for the $i^{th}$ variables.

In this way, in determining a partial position of any one of respective selected variables of nodes, the visualization device considers actual upper and lower limits of variable values for the respective selected variables of the nodes other than a range between an upper limit and a lower limit that are previously determined for the selected variable so that the nodes may be spaced apart from each other by a sufficient distance without being concentrated in a specific area in the 3D polygon.

Meanwhile, the $P\max_{(i)}$ and $P\min_{(i)}$ may be positions on a coordinate system 440 including an x-axis, a y-axis, and a z-axis shown in FIG. 4.

In operation S330, the visualization device determines final positions of the nodes in the 3D polygon based on partial positions respectively determined for the nodes. For example, the visualization device may determine respective partial positions related to height, weight, and blood pressure for the nodes, and then determine the final positions in the 3D polygon considering a relationship between the determined partial positions.

For example, the visualization device may respectively determine the final positions of the nodes according to Equation 2 below.

$$Np = \left(\sum_{i=1}^{c} Np_{(i)}\right) \div c \quad \text{[Equation 2]}$$

wherein, Np is a final position of any one of the nodes, i is any one of the variables, c is the number of the variables, and $Np_{(i)}$ is a partial position related to an $i^{th}$ variable of any one of the nodes.

In operation S340, the visualization device respectively arranges the nodes at the final positions in the 3D polygon. That is, the visualization device, according to the position of Np determined based on Equation 2 above, arranges corresponding nodes in the 3D polygon.

In operation S350, the visualization device displays the 3D polygon in which the nodes are arranged.

Figure 5:
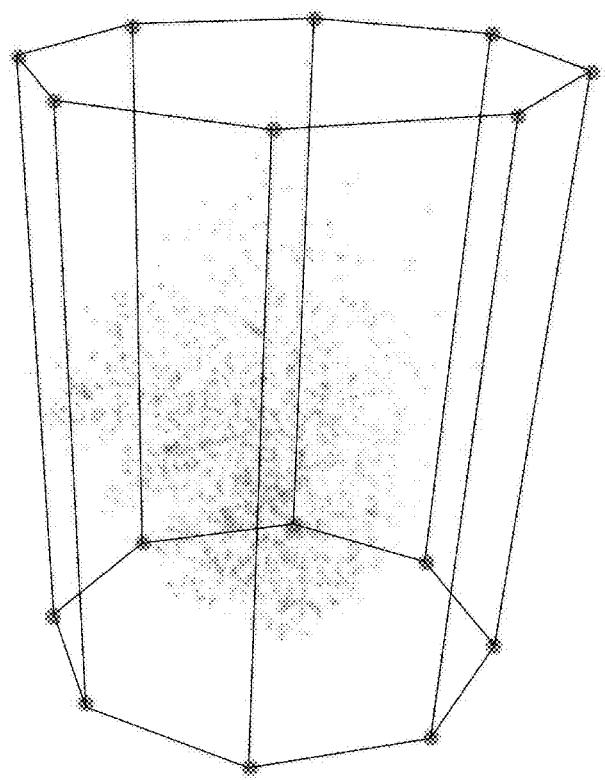
FIG. 5 is an exemplary view of a plurality of nodes arranged in a 3D polygon.

FIG. 5 illustrates a 3D polygon in which a plurality of nodes are arranged. As shown in FIG. 5, it can be seen that a large number of data nodes are widely distributed in a 3D space without being concentrated in the center.

A visualization device according to an example embodiment may cluster nodes arranged on the 3D polygon as shown in FIG. 5 to provide more useful information to a user.

Figure 6:
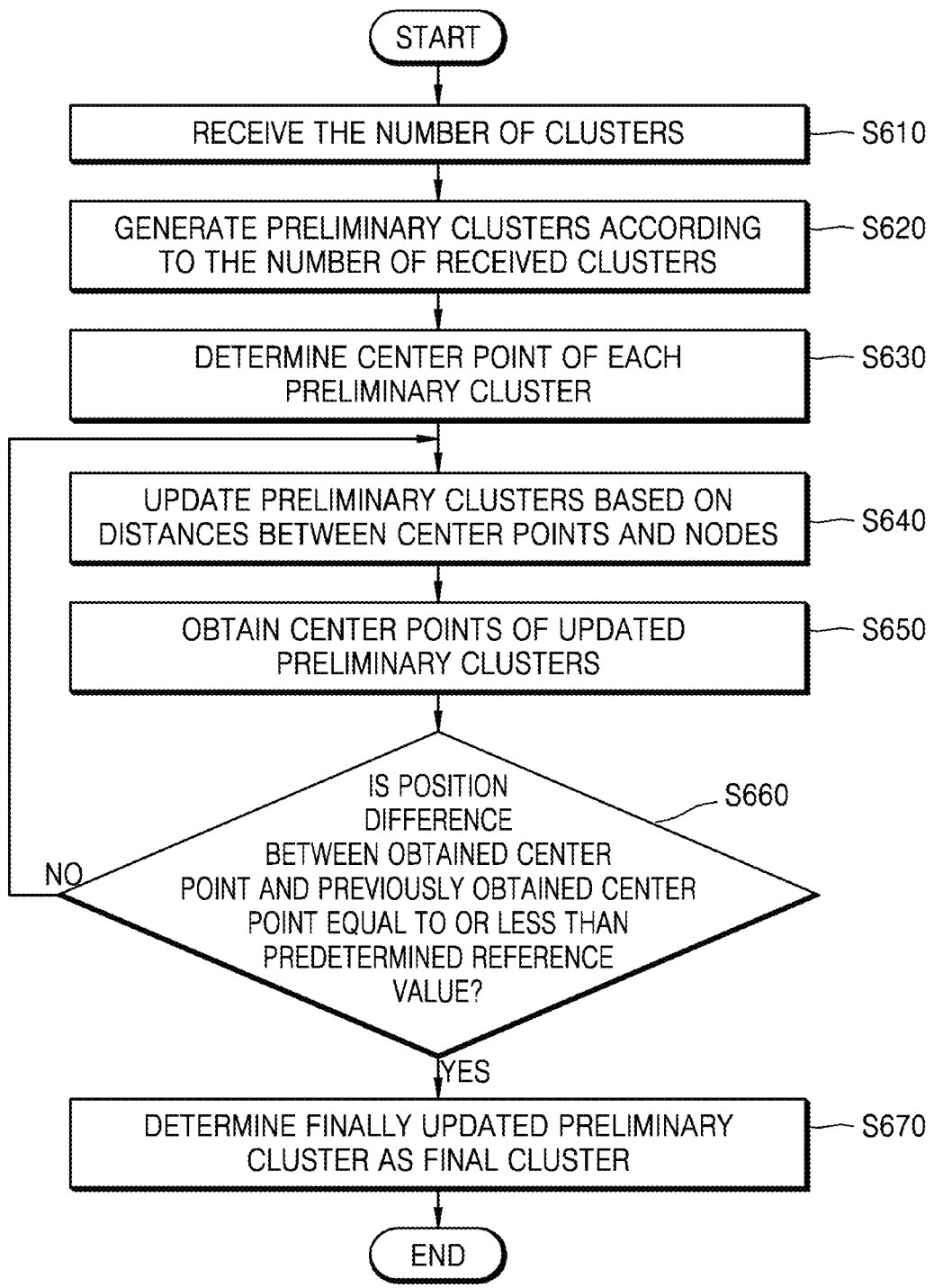
FIG. 6 is a flowchart of a clustering method according to an example embodiment.

FIG. 6 is a flowchart of a clustering method according to an example embodiment.

In operation S610, the visualization device receives the number of clusters from a user.

In operation S620, the visualization device generates a plurality of preliminary clusters according to the number of the received clusters. For example, the visualization device may divide the number of nodes arranged in a 3D polygon by the number of the received clusters, and arbitrarily group the number of nodes corresponding to the division result to generate a plurality of preliminary clusters. The visualization device may select an initial preliminary cluster through a Random algorithm or a Forgy algorithm. Since the Random algorithm generates an arbitrary center point of a cluster in the 3D polygon, different types of clusters may be generated each time clustering is performed. On the other hand, the Forgy algorithm proceeds by selecting the center point of the cluster as a specific node so that the same result may be obtained in clustering under the same condition. The Random algorithm and the Forgy algorithm are techniques obvious to those of ordinary skilled in the art, and thus, a detailed description thereof will not be given herein.

In operation S630, the visualization device determines a center point of each of the plurality of preliminary clusters. The visualization device may determine the center point of each of the plurality of preliminary clusters in various ways.

As a method, the visualization device may arbitrarily select one node in each of the plurality of preliminary clusters, and determine the selected node as a center point.

As another method, the visualization device may average positions of respective nodes included in the plurality of preliminary clusters to determine a center point of each of the preliminary clusters.

Alternatively, the visualization device may determine a specific node as a center point in consideration of a statistical position (e.g., regular distribution) of the respective nodes included in the plurality of preliminary clusters.

In operation S640, the visualization device may measure distances between the respective center points of the plurality of preliminary clusters and the nodes arranged in the 3D polygon, and may update the plurality of preliminary clusters based on the measured distances.

A distance between any one of the center points and any one of the nodes may be determined based on Equation 3 below.

$$D = \sqrt{(P_x - Q_x)^2 + (P_y - Q_y)^2 + (P_z - Q_z)^2} \quad \text{[Equation 3]}$$

wherein, D is a distance between a center point P and a node Q, $P_x$, $P_y$, and $P_z$ are an x-coordinate, a y-coordinate, and a z-coordinate of the center point P, and $Q_x$, $Q_y$, and $Q_z$ are an x-coordinate, a y-coordinate, and a z-coordinate of the node Q, respectively.

When distances between each center point and all the nodes are measured, the visualization device ensures that only nodes closest to each center point are included in the preliminary clusters. For example, if a first node is included in a first preliminary cluster and a distance between the first node and a center point of the first preliminary cluster is greater than a distance between the first node and a center point of a second preliminary cluster, the visualization device allows the first node to be included in the second preliminary cluster.

In operation S650, the visualization device obtains center points in a plurality of updated preliminary clusters.

The visualization device may determine the center points of the plurality of updated preliminary clusters based on Equation 4 below.

$$C = \frac{\sum_{i=1}^{n} Q_i}{n}$$ [Equation 4]

wherein, C is a center point of any one of the updated preliminary clusters, n is the number of nodes included in the updated preliminary cluster, and $Q_i$ is a position (i.e., coordinate) of the nodes included in the updated preliminary cluster.

In operation S660, the visualization device determines whether a position difference between a newly obtained center point and the previously obtained center point, i.e., the center point obtained in operation S630, is equal to or less than a predetermined reference value.

If the newly obtained center point and the previously obtained center point are larger than the reference value, the visualization device returns to operation S640 and updates each of the plurality of preliminary clusters based on distances between the newly obtained center point and the nodes, and in operation S650, obtains a center point again. That is, the visualization device repeats the process of updating the preliminary clusters and obtaining a new center point until the center point is not substantially changed.

In operation S670, if the position difference between the newly obtained center point and the previously obtained center point is equal to or less than the reference value, the visualization device determines a finally updated preliminary cluster as a final cluster.

The visualization device may distinguish and display the plurality of final clusters, for example, in different colors.

FIGS. 7A to 7D are exemplary views for explaining a clustering method according to an example embodiment in more detail.

Figure 7A:
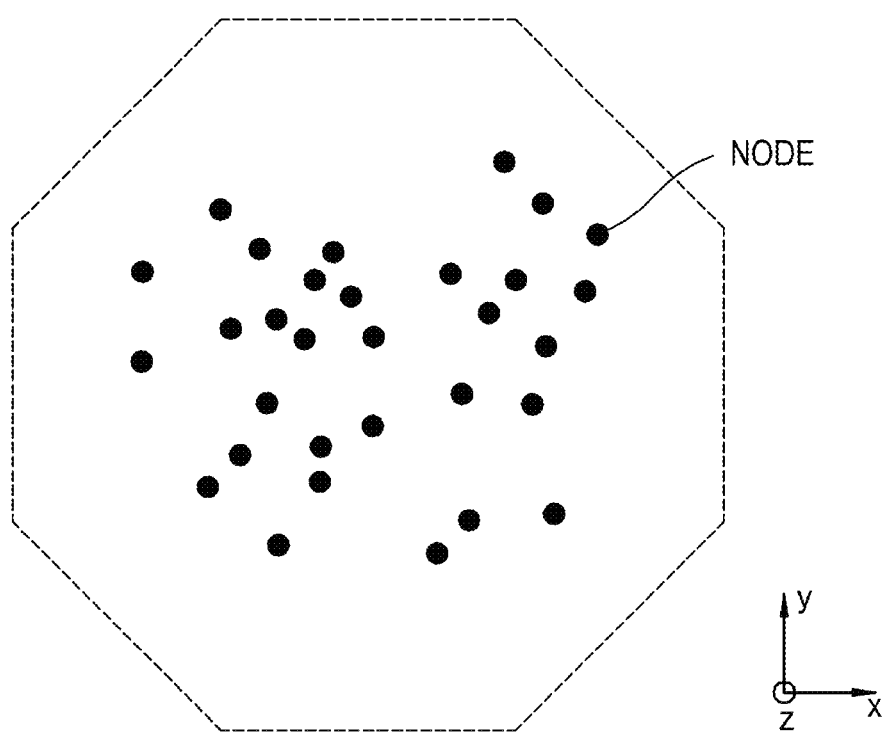
FIGS. 7A to 7D are exemplary views for explaining a clustering method according to an example embodiment.
Figure 7B:
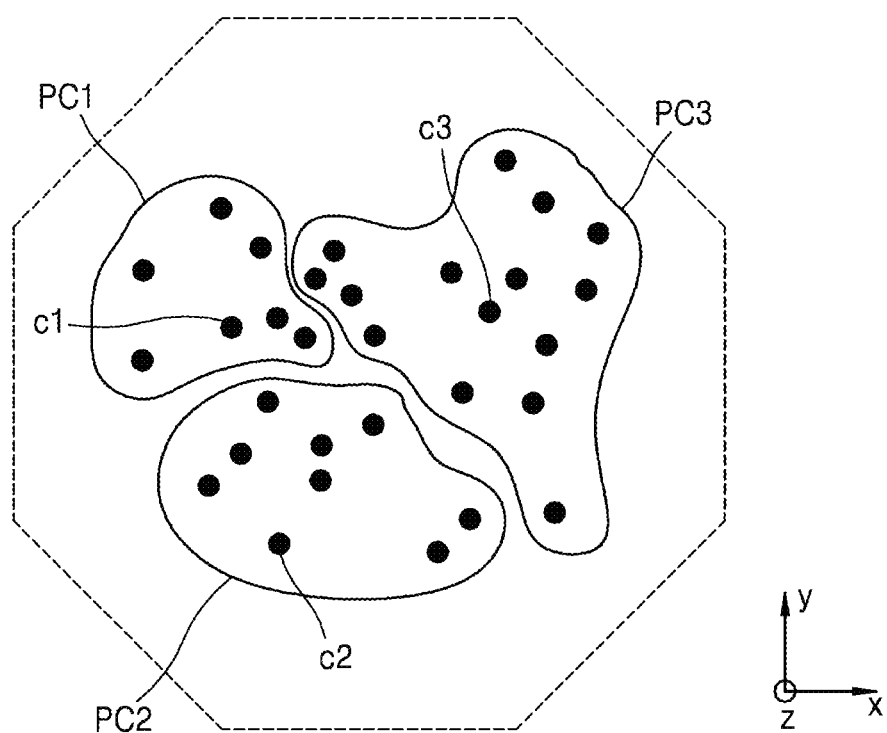

When nodes are arranged as shown in FIG. 7A, if a user inputs 3 as the number of clusters, the visualization device arbitrarily generates three preliminary clusters PC1, PC2, and PC3 as shown in FIG. 7B. Then, the visualization device determines center points c1, c2, and c3 in the preliminary clusters PC1, PC2, and PC3, respectively.

Figure 7C:
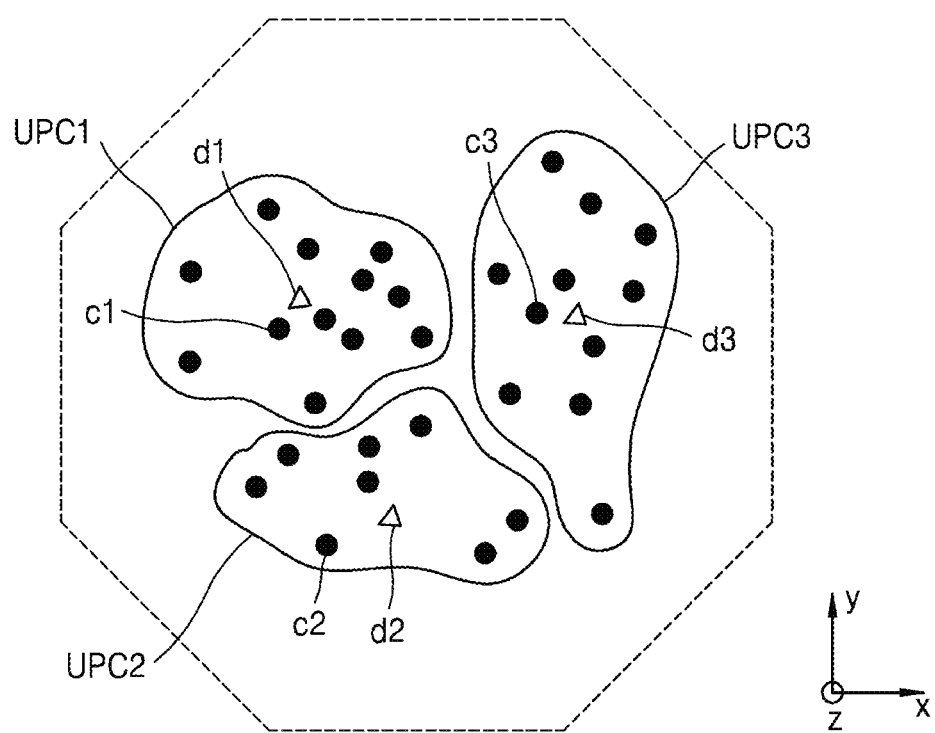

In FIG. 7C, the visualization device respectively updates the preliminary clusters PC1, PC2, and PC3 based on distances between the center points c1, c2, and c3 and each node. As a result, updated preliminary clusters UPC1, UPC2, and UPC3 are obtained as shown in FIG. 7C.

The visualization device obtains center points d1, d2 and d3 in the updated preliminary clusters UPC1, UPC2, and UPC3, respectively. Since the newly acquired center points d1, d2 and d3 are different from the previous center points c1, c2, and c3 (that is, mutual intervals exceed a predetermined reference value), the visualization device updates preliminary clusters based on distances between the center points d1, d2, and d3 and each node.

Figure 7D:
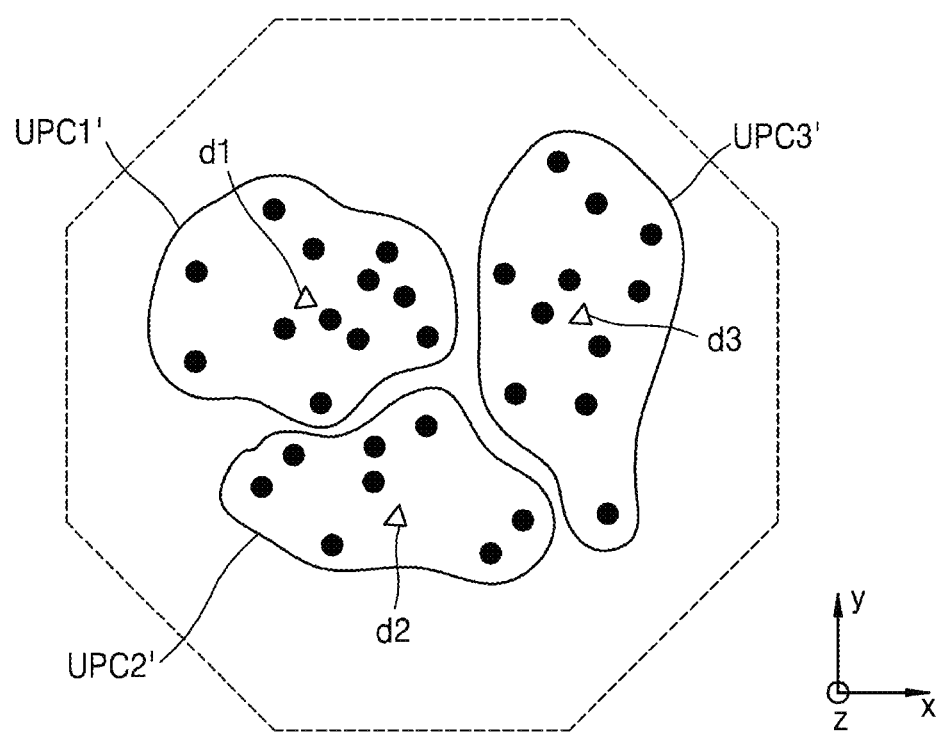

Center points d1, d2, and d3 of preliminary clusters UPC1', UPC2', and UPC3' shown in FIG. 7D are substantially equal to the previous center points d1, d2, and d3 (that is, mutual intervals exceed a predetermined reference value), the visualization device determines the preliminary clusters UPC1', UPC2', UPC3' shown in FIG. 7D as final clusters.

Figure 8:
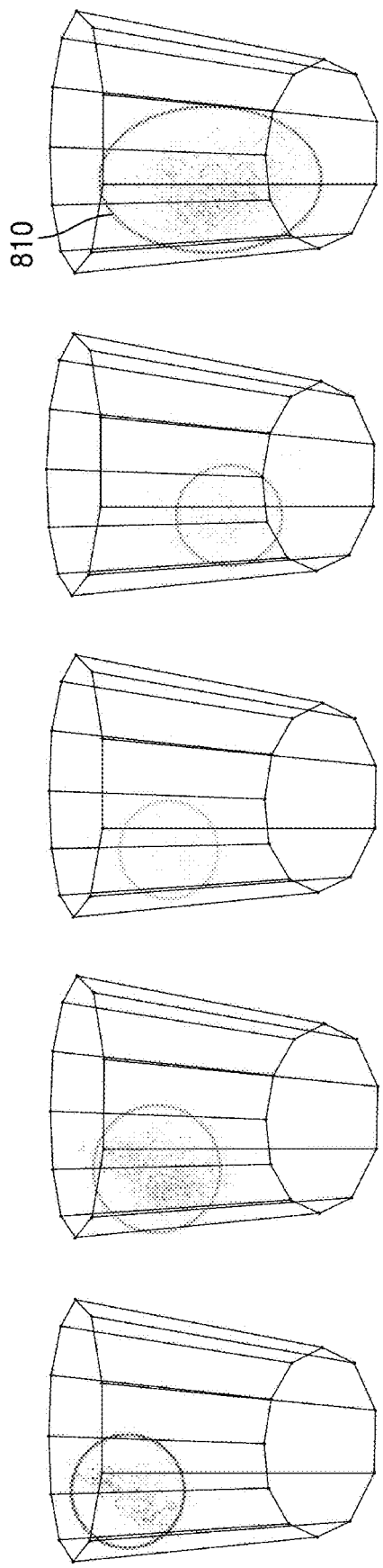
FIG. 8 is an exemplary view of a clustering result according to an example embodiment.

FIG. 8 is an exemplary view of a clustering result according to an example embodiment. It can be seen that nodes are widely distributed in a cluster 810 located at a rightmost of clusters in FIG. 8 compared to other clusters.

Figure 9:
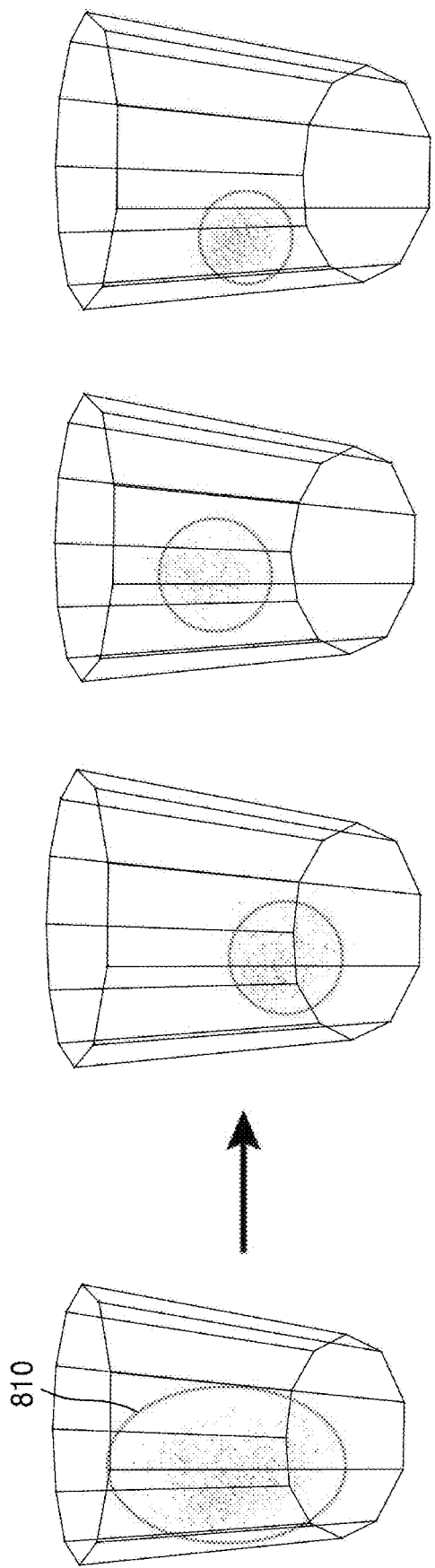
FIG. 9 is an exemplary view of sub-clusters divided from any one of clusters in FIG. 8.

Therefore, a visualization device according to an example embodiment may re-cluster clusters selected by a user from among the clusters. In more detail, the cluster 810 of FIG. 8 may be re-clustered as described in FIGS. 6 and 7A to 7D to determine a plurality of sub-clusters. Referring to FIG. 9, it can be seen that the cluster 810 of FIG. 8 is divided into three sub-clusters. However, the present disclosure is not limited thereto. According to an embodiment, the visualization device may estimate distribution intervals of the nodes in the clusters and re-cluster selected clusters according to the estimation result.

Meanwhile, the visualization device may distinguish (e.g., in different colors) and display a plurality of sub-clusters.

Figure 10:
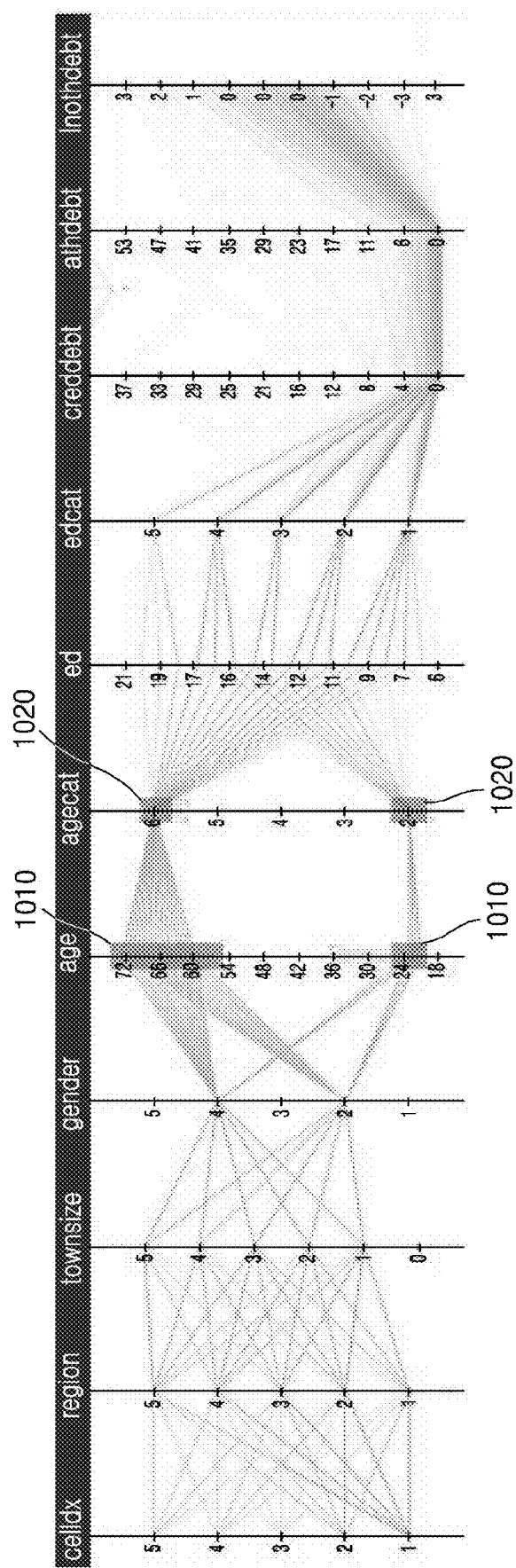
FIG. 10 is an exemplary view of a parallel coordinate graph according to an example embodiment.

FIG. 10 is an exemplary view of a parallel coordinate graph according to an example embodiment.

A visualization device may display variable values of at least one of nodes arranged in a 3D polygon as the parallel coordinate graph. For example, the visualization device may display variable values of a node selected by a user in the displayed 3D polygon as the parallel coordinate graph.

Furthermore, according to an example embodiment, the visualization device may receive a filtering range of a specific variable from a user. In this case, the visualization device may display nodes including only variable values included in the filtering range of the specific variable from among the nodes as the parallel coordinate graph.

As shown in FIG. 10, the visualization device may receive one or more filtering ranges 1010 for a specific variable, and may receive filtering ranges 1020 for one or more variables.

Figure 11:
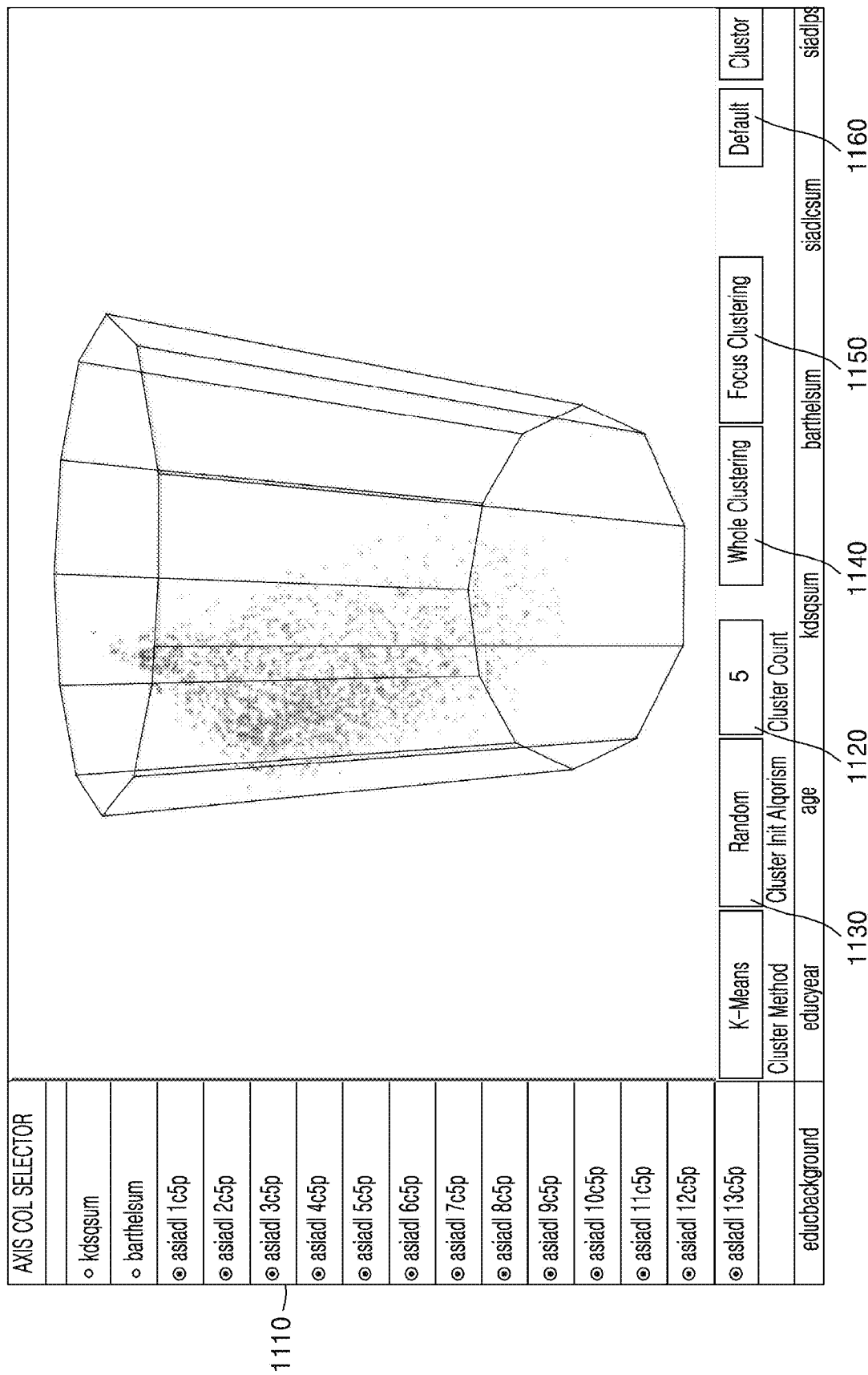
FIG. 11 is an exemplary view of a user interface according to an example embodiment.

FIG. 11 is an exemplary view of a user interface according to an example embodiment.

In reference numeral 1110 of FIG. 11, a user may select a variable to be viewed and display the variable on a 3D polygon. In addition, the user may select reference number 1120 to input the number of clusters, and the user may further select a clustering algorithm (Random algorithm or Forgy algorithm, etc.) by selecting reference numeral 1130. Reference numeral 1140 is a menu button for executing clustering, and reference numeral 1150 is an execution button for re-clustering a specific cluster. Reference numeral 1160 is a selection button for displaying the 3D polygon before clustering or after clustering on a screen.

As described above, the user may select specific nodes in the 3D polygon shown in FIG. 11 through a mouse drag or the like to view them in a separate 3D polygon. However, the present disclosure is not limited thereto. The user may enlarge and view the selected specific nodes in the displayed 3D polygon, or view them in a parallel coordinate graph or the like.

Figure 12:
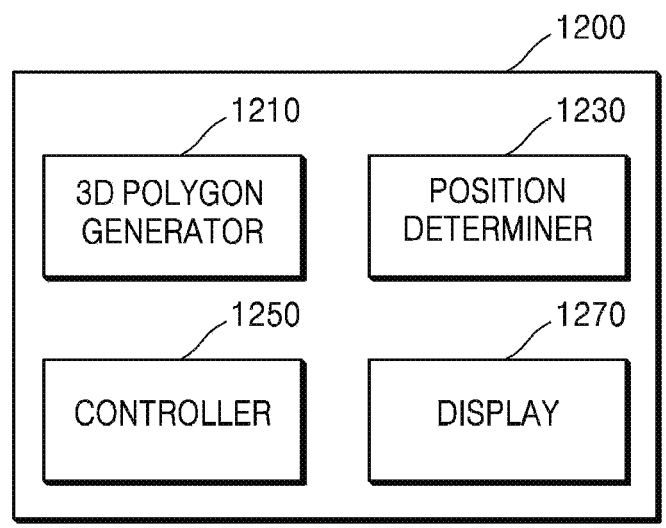
FIG. 12 is a block diagram of a partial configuration of a visualization device, according to an example embodiment.

FIG. 12 is a block diagram of a partial configuration of a visualization device 1200, according to an example embodiment.

Referring to FIG. 12, the visualization device 1200 according to an example embodiment may include a 3D polygon generator 1210, a position determiner 1230, a controller 1250, and a display 1270.

The 3D polygon generator 1210, the position determiner 1230, and the controller 1250 may be implemented by at least one processor or the like, and may operate according to a program stored in at least one memory (not shown).

The 3D polygon generator 1210 generates a 3D polygon based on a predetermined maximum value and a predetermined minimum value corresponding to each of a plurality of selected variables from among a plurality of variables. After generating the 3D polygon corresponding to the number of selected variables, the 3D polygon generator 1210 may arrange the predetermined maximum value and the predetermined minimum value at each vertex.

The position determiner 1230 determines partial positions related to variables respectively selected for a plurality of nodes, and determines a final position of each of the nodes in the 3D polygon based on the determined partial positions. The position determiner 1230 may respectively determine the partial positions related to the variables for the nodes based on an upper limit value and a lower limit value for each of the variables, a maximum variable value and a minimum variable value for each variable from among variable values of the nodes, and the variable values of the nodes, and may respectively determine the final positions of the nodes in the 3D polygon based on the determined partial positions. The position determiner 1230 may determine the partial positions according to Equation 1, and may determine the final positions according to Equation 2.

The controller 1250 arranges the plurality of nodes at the final positions in the 3D polygon, and the display 1270 displays the 3D polygon in which the plurality of nodes are arranged.

In addition, the controller 1250 may divide the nodes arranged in the 3D polygon into a plurality of clusters according to the number of clusters input by a user, and may display the nodes to be distinguished from each other and output the same through the display 1270.

Furthermore, the controller 1250 may display variable values of at least one of the nodes in the 3D data in a parallel coordinate and output the same through the display 1270. When a filtering range is selected by a user, nodes including variable values included in the filtering range may be displayed in the parallel coordinate.

According to one or more example embodiments, a method and a device for visualizing multi-dimensional data enable a user to more easily analyze multi-dimensional data.

Furthermore, according to one or more example embodiments, a method and a device for visualizing multi-dimensional data may effectively cluster multi-dimensional data.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the scope of the inventive concept as defined by the following claims.

What is claimed is:

1. A method of visualizing a plurality of nodes respectively comprising a plurality of variable values for a data object, the method comprising:

allocating a predetermined upper limit value and a predetermined lower limit value for each of a plurality of variables to vertices of a three-dimensional polygon facing each other;

respectively determining partial positions related to the variables for the nodes based on the upper limit value and the lower limit value for each of the variables, a maximum variable value and a minimum variable value for each variable from among variable values of the nodes, and the variable values of the nodes;

respectively determining final positions of the nodes in the three-dimensional polygon based on the determined partial positions; and arranging the nodes in the three-dimensional polygon according to the determined final positions, wherein the partial positions related to the variables for the nodes are more related to the maximum variable value and the minimum variable value for each variable from among the variable values of the nodes than the predetermined upper limit value and the predetermined lower limit value.

2. The method of claim 1, wherein the allocating to the vertices comprises selecting the variables by a user.

3. The method of claim 1, wherein the allocating to the vertices comprises allocating an upper limit value and a lower limit value for any one of the variables to an upper vertex and a lower vertex connected to each other by a side in the three-dimensional polygon, respectively.

4. The method of claim 1, further comprising:
displaying variable values included in the nodes in a parallel coordinate graph.

5. The method of claim 4, wherein the displaying in the parallel coordinate graph comprises:
receiving a filtering range for at least one variable from a user; and
displaying variable values included in the filtering range from among the variable values included in the nodes in the parallel coordinate graph.

6. The method of claim 5, wherein the filtering range is plural.

7. The method of claim 1, further comprising:
receiving the number of clusters from a user;
clustering the nodes arranged in the three-dimensional polygon according to the received number of the clusters; and
displaying the plurality of nodes that are clustered to be distinguished from each other.

8. The method of claim 7, wherein the clustering comprises:
arbitrarily clustering the nodes arranged in the three-dimensional polygon according to the received number of the clusters;
updating a plurality of preliminary clusters based on distances between respective center points of a plurality of preliminary clusters that are arbitrarily clustered and the nodes arranged in the three-dimensional polygon; and
repeatedly updating the plurality of preliminary clusters by comparing center points of the plurality of updated preliminary clusters with the center points of the plurality of preliminary clusters before updating, respectively.

9. The method of claim 8, wherein the repeatedly updating comprises repeatedly updating each of the plurality of preliminary clusters until the center point of each of the plurality of preliminary clusters is not changed.

10. The method of claim 7, further comprising:
re-clustering nodes included in clusters selected from among the clusters; and
displaying the nodes that are re-clustered as sub-clusters to be distinguished from each other.

11. The method of claim 10, wherein the re-clustering comprises:
receiving the number of the sub-clusters from the user; and
re-clustering the nodes included in the cluster selected from the clusters according to the received number of the sub-clusters.

12. A device for visualizing a plurality of nodes respectively comprising a plurality of variable values for a data object, the device comprising at least one processor and at least one memory implement to:
a three-dimensional polygon generator configured to allocate a predetermined upper limit value and a predetermined lower limit value for each of a plurality of variables to vertices of a three-dimensional polygon facing each other;
a position determiner configured to determine partial positions related to the variables for the plurality of nodes, respectively, and to determine a final position of each of the nodes in the three-dimensional polygon based on the determined partial positions; and
a controller configured to arrange the nodes in the three-dimensional polygon according to the determined final positions,
wherein the position determiner is configured to respectively determine the partial positions related to the variables for the nodes based on the upper limit value and the lower limit value for each of the variables, a maximum variable value and a minimum variable value for each variable from among variable values of the nodes, and the variable values of the nodes, and
wherein the partial positions related to the variables for the nodes are more related to the maximum variable value and the minimum variable value for each variable from among the variable values of the nodes than the predetermined upper limit value and the predetermined lower limit value.

13. The device of claim 12, further comprising:
a display configured to display the three-dimensional polygon in which the nodes are arranged.

* * * * *